(12) United States Patent
Sawada et al.

(10) Patent No.: US 7,622,043 B2
(45) Date of Patent: Nov. 24, 2009

(54) DIALYSIS DEVICE AND METHOD FOR CLEANING THE SAME

(75) Inventors: Toshiharu Sawada, Ishikawa-Ken (JP); Takashi Mishima, Ishikawa-Ken (JP)

(73) Assignee: Shibuya Kogyo Co., Ltd., Kanazawa-Shi, Ishikawa-Ken (JP)

( * ) Notice: Subject to any disclaimer, the term of this patent is extended or adjusted under 35 U.S.C. 154(b) by 263 days.

(21) Appl. No.: 11/789,305

(22) Filed: Apr. 24, 2007

(65) Prior Publication Data

US 2008/0041787 A1 Feb. 21, 2008

(30) Foreign Application Priority Data

Jun. 30, 2006 (JP) .............................. 2006-182433

(51) Int. Cl.
*B01D 61/30* (2006.01)
*B01D 61/24* (2006.01)
*B01D 35/14* (2006.01)
*B01D 61/26* (2006.01)

(52) U.S. Cl. ........................ 210/636; 210/645; 210/646; 210/739; 210/746; 210/749; 422/1; 422/28

(58) Field of Classification Search ................. 210/636, 210/645, 646, 739, 749, 321.69, 746; 422/1, 422/28

See application file for complete search history.

(56) References Cited

U.S. PATENT DOCUMENTS 3,441,136 A * 4/1969 Wilson, Jr. et al. ............. 210/90
3,753,493 A * 8/1973 Mellor ........................ 210/140
3,871,913 A * 3/1975 Shaldon .................... 134/22.18
4,153,554 A * 5/1979 von der Heide et al. ..... 210/96.2
4,166,031 A * 8/1979 Hardy ....................... 134/22.17
4,618,343 A * 10/1986 Polaschegg .................. 604/29
4,718,022 A * 1/1988 Cochran ................. 210/321.71
4,731,731 A * 3/1988 Cochran ...................... 210/739
4,789,467 A * 12/1988 Lindsay et al. ............... 210/103
5,759,489 A * 6/1998 Miura et al. .................. 422/28

FOREIGN PATENT DOCUMENTS

JP 2001-009029 1/2001

OTHER PUBLICATIONS

English Translation of Japanese Publication No. 2001-009029.*

* cited by examiner

*Primary Examiner*—John Kim
(74) *Attorney, Agent, or Firm*—Flynn, Thiel, Boutell & Tanis, P.C.

(57) ABSTRACT

In cleaning the dialysis device, first, the concentrate passage is disconnected from the dialysis solution concentrate container and is connected to the branched passage, and a precleaning process is performed in which the fluid circuit is replace with the purified water, and determining means (4a) of a control device (4) determines that the fluid circulating in the fluid circuit is not the dialysis solution by using a conductivity meter (29), and also determines that gas is not contained in the fluid circuit by using a downward movement detecting sensor 34b in a deaeration tank, and then a main cleaning process is performed by using a cleaning solution. Incomplete cleaning due to incomplete connection can be prevented.

3 Claims, 2 Drawing Sheets

DIALYSIS DEVICE AND METHOD FOR CLEANING THE SAME

BACKGROUND OF THE INVENTION

1. Field of the Invention

The present invention relates to a dialysis device and a method for cleaning the same, in particular to a dialysis device and a method for cleaning the same in which a concentrate passage is provided on a fluid supplying side of a fluid circuit which is connected to a dialyser, and the concentrate passage joins the fluid circuit and is connected to a dialysis solution concentrate container, so that a dialysis solution is prepared in the fluid circuit.

2. Description of the Related Art

Conventionally, a personal dialysis device for preparing a dialysis solution therein is configured to include a dialyser, a fluid circuit which is connected to the dialyser, and a concentrate passage provided on a fluid supplying side of the fluid circuit which joins the fluid circuit and is connected to a dialysis solution concentrate container, so that purified water is supplied through a water inlet of the fluid circuit and a dialysis solution concentrate is supplied through the concentrate passage to prepare a dialysis solution in the fluid circuit to be supplied to the dialyser.

In such a dialysis device, since the fluid circuit has to be cleaned every time a dialysis treatment is completed, a cleaning port section (cleaning solution supplying section) is provided for supplying a cleaning solution to the concentrate passage, and when a dialysis treatment is completed, the concentrate passage is disconnected from the dialysis solution concentrate container and is connected to the cleaning port section to make the cleaning solution supplied to the fluid circuit via the concentrate passage, which allows the cleaning solution to be supplied to the concentrate passage (see Japanese Patent Laid-Open No. 2001-9029).

However, because the disconnection and connection of the concentrate passage from the dialysis solution concentrate container to the cleaning port section is manually performed, the concentrate passage may fail to be disconnected and remains to be connected to the dialysis solution concentrate container, or a cleaning process may be started with the concentrate passage being imperfectly connected to the dialysis solution concentrate container, which raises a possibility that the cleaning process will be ended without a supply of the cleaning solution to the concentrate passage.

SUMMARY OF THE INVENTION

The present invention was made in view of the above situation, and one object of the present invention is to provide a dialysis device and a method for cleaning the same in which an incomplete cleaning process due to incomplete disconnection and connection of a concentrate passage from a dialysis solution concentrate container to a cleaning port section is prevented, and such an incomplete connection if any is promptly found.

That is, a dialysis device comprises: a fluid circuit which is connected to a dialyser; A concentrate passage provided on a fluid supplying side of the fluid circuit which joins the fluid circuit and is connected to a dialysis solution concentrate container, thereby purified water is supplied through a water inlet of the fluid circuit and a dialysis solution concentrate is supplied through the concentrate passage to prepare a dialysis solution in the fluid circuit to be supplied to the dialyser;

a cleaning solution supplying section to which the concentrate passage is connected for supplying a cleaning solution to the concentrate passage, so that during a dialysis treatment, the concentrate passage is connected to the dialysis solution concentrate container to supply a dialysis solution concentrate through the concentrate passage to the fluid circuit, and during a cleaning process of the fluid circuit after the dialysis treatment, the concentrate passage is disconnected from the dialysis solution concentrate container and is connected to the cleaning solution supplying section to supply the cleaning solution to the concentrate passage;

characterized in that a dialysis solution detector for detecting a circulation of the dialysis solution at a position downstream of the junction of the concentrate passage with the fluid circuit; and determining means to which a detection signal from the dialysis solution detector is input, and the determining means determines that the concentrate passage is connected to the dialysis solution concentrate container when the dialysis solution detector detects a circulation of the dialysis solution and/or dialysis solution concentrate during the cleaning process.

Also, a dialysis device comprises: a fluid circuit which is connected to a dialyser; A concentrate passage provided on a fluid supplying side of the fluid circuit which joins the fluid circuit and is connected to a dialysis solution concentrate container, thereby purified water is supplied through a water inlet of the fluid circuit and a dialysis solution concentrate is supplied through the concentrate passage to prepare a dialysis solution in the fluid circuit to be supplied to the dialyser;

a cleaning solution supplying section to which the concentrate passage is connected for supplying a cleaning solution to the concentrate passage, so that during a dialysis treatment, the concentrate passage is connected to the dialysis solution concentrate container to supply a dialysis solution concentrate through the concentrate passage to the fluid circuit, and during a cleaning process of the fluid circuit after the dialysis treatment, the concentrate passage is disconnected from the dialysis solution concentrate container and is connected to the cleaning solution supplying section to supply the cleaning solution to the concentrate passage;

characterized in that a gas detector for detecting gas in the fluid circuit at a position downstream of the junction of the concentrate passage with the fluid circuit; and determining means to which a detection signal from the gas detector is input, and the determining means determines that the concentrate passage is imperfectly connected to the cleaning solution supplying section when the gas detector detects a predetermined amount of gas in the fluid circuit during the cleaning process.

Furthermore, a method for cleaning dialysis device which comprises a fluid circuit which is connected to a dialyser, A concentrate passage provided on a fluid supplying side of the fluid circuit which joins the fluid circuit and is connected to a dialysis solution concentrate container, thereby purified water is supplied through a water inlet of the fluid circuit and a dialysis solution concentrate is supplied through the concentrate passage to prepare a dialysis solution in the fluid circuit to be supplied to the dialyser and a cleaning solution supplying section to which the concentrate passage is connected for supplying a cleaning solution to the concentrate passage, comprising the steps of:

during a dialysis treatment, connecting the concentrate passage to the dialysis solution concentrate container to supply the dialysis solution concentrate through the concentrate passage to the fluid circuit;

after the dialysis treatment, during a cleaning process of the fluid circuit, disconnecting the concentrate passage from the dialysis solution concentrate container and connecting the concentrate passage to the cleaning solution supplying section to supply the cleaning solution through the concentrate passage;

characterized in that during a pre-cleaning process before the cleaning process in which the cleaning solution is circulated to the fluid circuit, circulating purified water through the fluid circuit to replace the dialysis solution remaining in the fluid circuit with the purified water, so that a state of the connection between the concentrate passage and the cleaning solution supplying section is checked.

Figure 1:
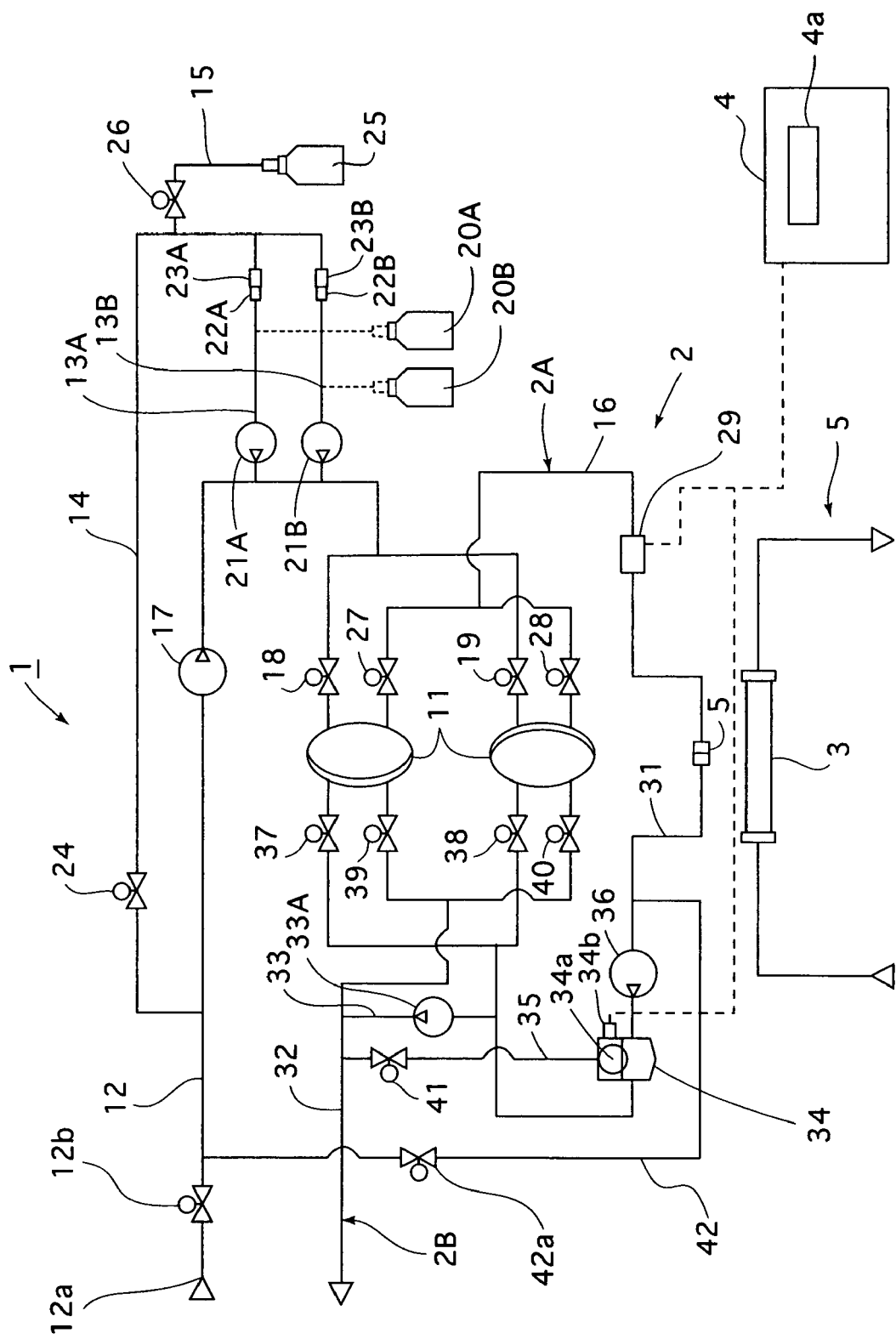
FIG. 1 is a view showing a fluid circuit of a dialysis device of an embodiment.

DESCRIPTION OF SYMBOLS 1 dialysis device
2 fluid circuit
11 measuring chamber
12 water supply passage
13A, 13B concentrate passage
14 branched passage
15 cleaning solution passage
20A, 20B dialysis solution concentrate container
22A, 22B connector
23A, 23B coupler
29 conductivity meter
34 deaeration tank
34b downward movement detecting sensor

DETAILED DESCRIPTION OF THE PREFERRED EMBODIMENT

Now, an embodiment will be explained below with reference to the drawings. FIG. 1 and FIG. 2 show a dialysis device 1 of the embodiment, and FIG. 1 shows a fluid circuit 2 which is provided inside of a body of the dialysis device 1, while FIG. 2 shows an outside of the dialysis device 1.

The fluid circuit 2 is connected to a dialyser 3 for supplying a dialysis solution to the dialyser 3 and discharging the dialysis solution from the dialyser 3, and is consisted of fluid passages which are formed of tubular members. The fluid passages are provided with various solenoid valves and pumps which are configured to be controlled by a control device 4 included in the dialysis device 1.

The dialyser 3 is disposed in a blood circuit 5 outside of the dialysis device 1, and includes a number of bundled hollow fibers therein so that blood flows through the hollow fibers in a direction to the right side of FIG. 1 and the dialysis solution flows outside of the hollow fibers in a direction to the left side of FIG. 1 which is opposite to that of the blood.

Figures 2A, 2B:
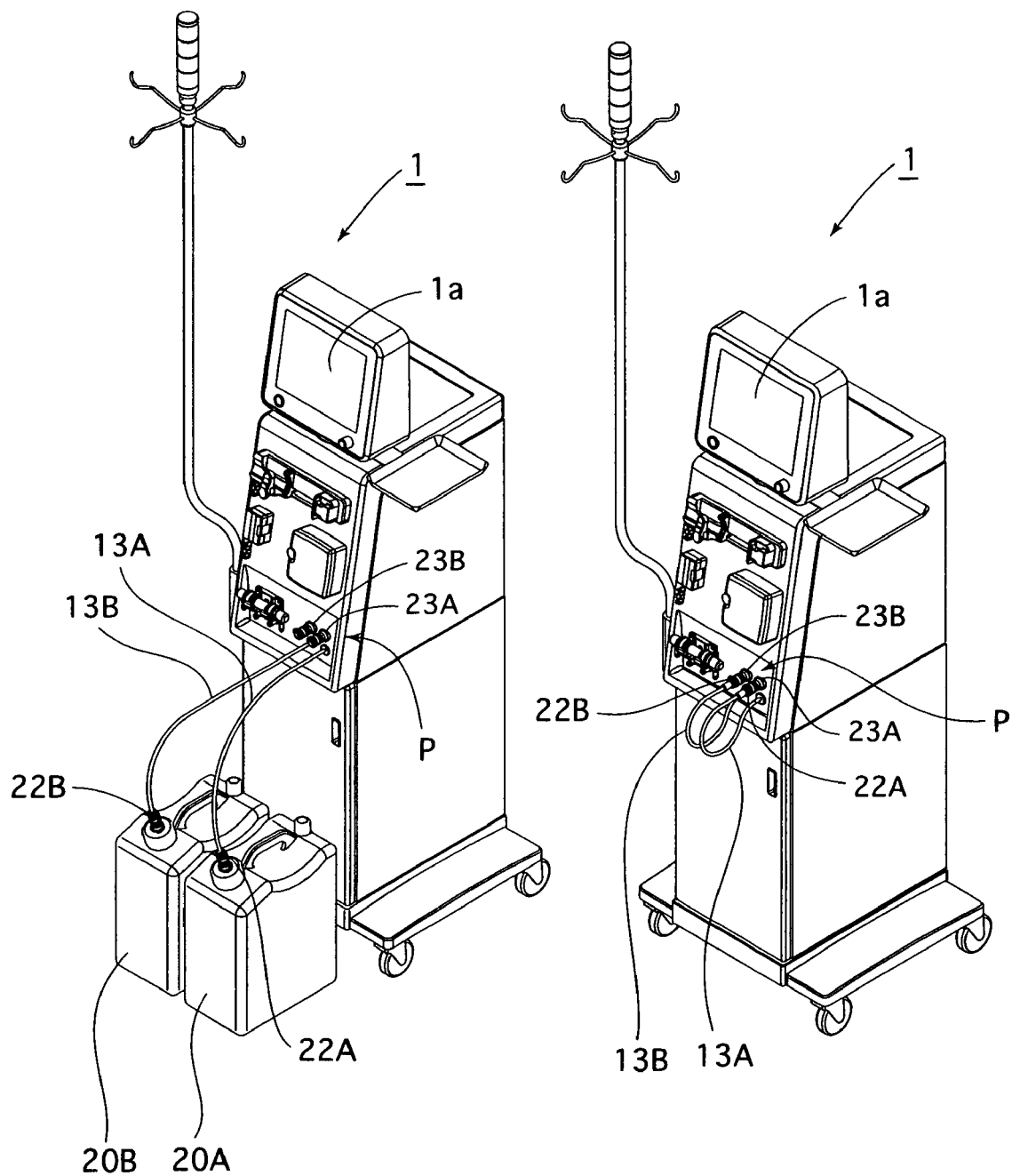
FIGS. 2(A) and 2(B) are perspective views showing a dialysis device during a dialysis operation and during a cleaning operation, respectively.

FIG. 1 shows the fluid circuit 2 in a cleaning process, with the dialyser 3 being removed from the fluid circuit 2, and a tail end on a fluid supplying side being coupled with a distal end on a fluid discharging side. FIG. 2(A) shows the dialysis device 1 in a dialysis treatment (the dialyser 3 and the blood circuit 5 are not shown), and FIG. 2(B) shows the dialysis device 1 in a cleaning process of the fluid circuit 2.

The fluid circuit 2 includes a fluid supplying circuit 2A for preparing a dialysis solution and supplying the prepared new dialysis solution to the dialyser 3, a fluid discharging circuit 2B disposed downstream of the fluid supplying circuit 2A for discharging a processed dialysis solution from the dialyser 3, and two measuring chambers 11 inside of which are individually divided into a fluid supply chamber and a fluid discharge chamber by a bellowphragm for measuring the amount of the new dialysis solution supplied to the dialyser 3 and the amount of the processed dialysis solution discharged from the dialyser 3.

The fluid supplying circuit 2A includes: a water supply passage 12 for supplying purified water to the fluid supply chambers in each measuring chamber 11; concentrate passages 13A, 13B which join the water supply passage 12 for supplying a dialysis solution concentrate; a branched passage 14 which is branched from the water supply passage 12 at a position upstream of the junction of the concentrate passage 13A, 13B with the water supply passage 12 for circulating the purified water; a cleaning solution passage 15 which joins the branched passage 14 for supplying a cleaning solution; and a fluid supply passage 16 for supplying the dialysis solution to the dialyser 3 after a mixing process at the measuring chamber 11.

The water supply passage 12 includes a water inlet 12a connected to purified water supplying means (not shown), and downstream of the water inlet 12a is provided with a water supply solenoid valve 12b so that opening of the water supply solenoid valve 12b allows purified water to be supplied to the water supply passage 12. A fluid supply pump 17 is disposed downstream of the water supply solenoid valve 12b to feed the supplied purified water toward further downstream.

The water supply passage 12 downstream of the fluid supply pump 17 is branched to be connected to each of the measuring chambers 11, and the branched portions are provided with a first solenoid valve 18 and a second solenoid valve 19 for each of the measuring chambers 11 respectively, so that the solenoid valve 18 and 19 are alternately opened and closed to supply the purified water to each of the corresponding measuring chambers 11.

The concentrate passages 13A and 13B join the water supply passage 12, and one ends of the concentrate passages 13A and 13B are connected to the water supply passage 12 on an upstream side of position where the water supply passage 12 is branched into two for each of the measuring chambers 11, and the other tip ends of the concentrate passages 13A and 13B are, as shown in FIG. 2, taken out of the body of the dialysis device 1, so as to connect the concentrate passage 13A to a dialysis solution concentrate container 20A in which an A concentrate is stored as a dialysis solution concentrate, and connect the concentrate passage 13B to a dialysis solution concentrate container 20B in which a B concentrate is stored.

Each of the concentrate passages 13A and 13B are provided with concentrate feed pumps 21A and 21B respectively for feeding a dialysis solution concentrate at a position upstream of the junction thereof with the water supply passage 12.

The tip ends of the concentrate passages 13A and 13B are provided with connectors 22A and 22B respectively as connecting means so as to be connected to couplers 23A and 23B provided to the branched passage 14, which will be explained later.

In operating the dialysis device 1 for dialysis, as shown by broken lines in FIG. 1, the concentrate passages 13A and 13B are connected to the dialysis solution concentrate containers 20A and 20B respectively, so that the operation of the concentrate feed pumps 21A and 21B causes a fixed amount of the A concentrate and a fixed amount of the B concentrate to be supplied to the water supply passage 12.

The branched passage 14 is branched from the water supply passage 12 at a position upstream of the fluid supply pump 17, and is provided with a third solenoid valve 24. The branched passage 14 is further branched at the tip end into two passages having ends to which the couplers 23A and 23B are provided.

The couplers 23A and 23B are, as shown in FIG. 2, mounted on and protruded outward from the body surface of the dialysis device 1, and form a cleaning port P as a cleaning solution supplying section, so as to be connected to the connectors 22A and 22B of the concentrate passages 13A and 13B outside of the body of the dialysis device 1.

The branched passage 14 is also connected to a cleaning solution container 25 in which a cleaning solution is stored, via the cleaning solution passage 15, and the cleaning solution passage 15 is provided with a fourth solenoid valve 26 which is opened in a cleaning process of the fluid circuit 2.

In operating the dialysis device 1 for cleaning, as shown in FIG. 1 or FIG. 2(B), the connectors 22A and 22B of the concentrate passages 13A and 13B are connected to the couplers 23A and 23B of the branched passages 14 respectively to make the concentrate passages 13A and 13B being communicated with the branched passage 14, thereby purified water can be supplied to each of the concentrate passages 13A and 13B via the branched passage 14, or a cleaning solution in the cleaning solution container 25 can be supplied by opening the fourth solenoid valve 26.

The fluid supply passage 16 is connected to the fluid supply chambers in each of the measuring chambers 11, and are merged into one to be connected to the dialyser 3. The measuring chambers 11 are provided with fifth and sixth valves 27 and 28 respectively, and an alternate opening and closing of the valves 27 and 28 causes a dialysis solution to be supplied to the dialyser 3 through the fluid supply passage 16.

The fluid supply passage 16 is positioned downstream of the junctions of each of the concentrate passages 13A and 13B with the fluid circuit 2, and is provided with a conductivity meter 29 as a dialysis solution detector for detecting a circulation of a dialysis solution.

The conductivity meter 29 is configured to detect a circulation of a dialysis solution, by detecting a conductivity of the fluid flowing through the fluid supply passage 16 and outputting a detection signal to the control device 4 to cause the control device 4 to measure a conductivity of the fluid based on the signal and to determine if the resulting value falls in a range for a dialysis solution.

The above described fluid discharging circuit 2B includes: a collection passage 31 for collecting the processed dialysis solution which is discharged from the dialyser 3 into the fluid discharge chambers in each of the measuring chambers 11; a discharge passage 32 for discharging the processed dialysis solution from the fluid discharge chambers in each of the measuring chambers 11 to the outside of the dialysis device 1; and a water removal passage 33 for making the collection passage 31 being communicated with the discharge passage 32, the water removal passage 33 being provided with a water removal pump 33A so that the operation of the water removal pump 33A causes water to be removed during a dialysis treatment.

The collection passage 31 is connected to the dialyser 3, and also is branched into two to be connected to the fluid discharge chambers in each of the measuring chambers 11, with the branched portions being provided with seventh and eighth solenoid valves 37 and 38 respectively so that an alternative opening and closing of the solenoid valves 37 and 38 causes each of the measuring chambers 11 to collect the processed dialysis solution.

The collection passage 31 is provided with a feed pump 36 and a deaeration tank 34 downstream of the feed pump 36, and an air exhaustion passage 35 connects between the deaeration tank 34 and the discharge passage 32, and the air exhaustion passage 35 is provided with an eleventh solenoid valve 41.

A cleaning passage 42 connects the upstream side of the feed pump 36 and the downstream side of the water supply solenoid valve 12b in the water supply passage 12, thereby, in cleaning the fluid circuit 2, the water supply solenoid valve 12b is closed and the communicating solenoid valve 42a in the cleaning passage 42 is opened to feed a cleaning solution from the collection passage 31 to the water supply passage 12.

The discharge passage 32 is connected to the fluid discharge chambers in each of the measuring chambers 11, and are also merged into one to be open to the outside of the dialysis device 1, thereby an alternative opening and closing of ninth and tenth solenoid valves 39 and 40 which are provided to the discharge passage 32 corresponding to each measuring chamber 11 causes the processed dialysis solution to be discharged from each measuring chamber 11.

The deaeration tank 34 includes a float needle valve 34a therein which moves downward with a fluid level when gas is released from the fluid flown into the deaeration tank 34, which makes the inside of the deaeration tank 34 being communicated with an air exhaustion passage 35.

The deaeration tank 34 further includes a downward movement detecting sensor 34b for detecting a downward movement of the float needle valve 34a by a predetermined amount; so that when a predetermined amount of air is released into the deaeration tank 34 and the float needle valve 34a moves downward, the downward movement detecting sensor 34b detects the movement and outputs a detection signal to the control device 4.

Upon receiving the detection signal, the control device 4 detects a contamination of a predetermined amount of gas into the fluid circuit 2, and generates an alert and also opens the eleventh solenoid valve 41 to discharge the gas from the deaeration tank 34.

The deaeration tank 34 is disposed downward of the junction of the concentrate passage 13A and 13B with the fluid circuit 2, and is configured as a gas detector for detecting gas in the fluid circuit 2.

The control device 4 includes determining means 4a for determining a state of the connection, in operating the dialysis device 1 for dialysis, between the connectors 22A and 22B of each of the concentrate passages 13A and 13B and the couplers 23A and 23B at the cleaning port P which provides a cleaning solution supplying section.

The determining means 4a is enabled in a cleaning mode in which the control device 4 implements a cleaning operation, and determines states of the changed connections of each of the concentrate passages 13A and 13B during a cleaning operation, by receiving detection signals from the conductivity meter 29 and the downward movement detecting sensor 34b in the deaeration tank 34, and generates an alert signal for an incomplete connection.

Next, a method for cleaning the dialysis device 1 of the embodiment will be explained below.

When a dialysis treatment is completed, a healthcare professional removes a blood circuit 5 from a patient, separates the dialyser 3 from the fluid circuit 2, and couples the tail end of the fluid supply passage 16 to the distal end of the collection passage 31 by using the connector.

As shown in FIG. 2(B), the healthcare professional also removes the connectors 22A and 22B of each of the concentrate passages 13A and 13B from the dialysis solution concentrate containers 20A and 20B, and connects them to the couplers 23A and 23B of the branched passages 14 which are provided as a cleaning port P, thereby the concentrate passages 13A and 13B are connected to the branched passages 14.

After completing these works, when the healthcare professional operates an operation panel 1a to specify a cleaning of the fluid circuit 2, the control device 4 is transferred to a cleaning mode to start a cleaning operation. In the cleaning operation, the control device 4 first performs a pre-cleaning process by discharging and replacing the dialysis solution, which is remained in the fluid circuit 2, with purified water.

Specifically, with the third solenoid valve 24 of the branched passage 14 being opened, similar to a normal dialysis operation, the water supply solenoid valve 12b is opened to flow the purified water through the water inlet 12a, and at the same time the fluid supply pump 17, the feed pump 36, the water removal pump 33A are operated, and each of the solenoid valves 18, 19, 27, 28, 37, 38, 39, and 40 is opened or closed, so that purified water is fed to the water supply passage 12, the fluid supply chambers in each of the measuring chamber 11, the fluid supply passage 16, the collection passage 31, the fluid discharge chambers in each of the measuring chamber 11, the discharge passage 32, the water removal passage 33, thereby the dialysis solution remained in the fluid circuit 2 is discharged and replaced with the purified water.

Each of the concentrate passages 13A and 13B is connected to the connectors 22A and 22B via the couplers 23A and 23B respectively, and the operations of each of the concentrate feed pumps 21A and 21B allow the purified water to flow into the branched passage 14 via the opened third solenoid valve 24 and to be supplied to each of the concentrate passages 13A and 13B.

As a result, the dialysis solution remaining in each of the concentrate passages 13A and 13B is also discharged and replaced with the purified water.

In the pre-cleaning process, the fourth solenoid valve 26 is not opened, and no cleaning solution is supplied.

In the above described pre-cleaning process, the control device 4 already enabled the determining means 4a, and causes detection signals from the conductivity meter 29 and the downward movement detecting sensor 34b of the deaeration tank 34 to be input to the determining means 4a.

The determining means 4a measures a conductivity based on the detection signal from the conductivity meter 29 at the point of time when the fluid supply passage 16 is filled with purified water after the pre-cleaning process starts, and detects a circulation of a dialysis solution when the measured result reaches a predetermined conductivity value which shows a presence of the dialysis solution. Upon the detection of the circulation of a dialysis solution, the determining means 4a determines that at least one of the concentrate passage 13A and concentrate passage 13B is still connected to the dialysis solution concentrate containers 20A and 20B, and generates an alert signal.

If only one of the A concentrate and the B concentrate stored in the dialysis solution concentrate containers 20A and 20B respectively is supplied, the conductivity measured by the fluid circuit 2 will be lower than that of the mixture of the A concentrate and the B concentrate, thereby the determining means 4a is set to have a conductivity value lower than a lower one of the conductivity values of the A and B concentrates so that the determining means 4a detects a circulation of a dialysis solution upon a measure of a conductivity equal to or more than the set value, as in the dialysis operation.

Meanwhile, the determining means 4a has monitored a detection signal from the downward movement detecting sensor 34b since the pre-cleaning process started, and upon receiving a detection signal, determines that a predetermined amount of gas is contained in the fluid circuit 2. That is, if at least one of the connectors 22A and 22B for the concentrate passages 13A and 13B is not completely connected to the couplers 23A and 23B of the branched passages 14, due to the suction of the concentrate feed pump 21, external air flows into the concentrate passages 13A and 13B and then into the purified water which is circulating in the fluid circuit 2.

Thus, upon a detection of the gas contamination, the determining means 4a determines that at least one of the connectors 22A and 22B for the concentrate passages 13A and 13B is not completely connected to the cleaning port P which provides a cleaning solution supplying section, and generates an alert signal.

Receiving any one of the above signals, the control device 4 displays an alert informing of an incomplete connection, and stops the pre-cleaning process. Then the healthcare professional fixes the incomplete connection of the concentrate passage 13A or the concentrate passage 13B according to the alert, and restarts the pre-cleaning process.

When the pre-cleaning process is completed after the check of the connection between the concentrate passages 13A and 13B and the cleaning port P, and the fixing the connection upon detection of an incomplete connection and the restarting and completing of the pre-cleaning process by a healthcare professional without more detection of another incomplete connection, the control device 4 immediately closes the third solenoid valve 24, and transfers to a main cleaning process.

In the main cleaning process, the control device 4 stops the liquid supply pump 36 and the water removal pump 33A and opens the fourth solenoid valve 26 in the cleaning solution passage 15, thereby due to the suction of the concentrate feed pumps 21A and 21B, a cleaning solution stored in the cleaning solution container 25 is supplied through the branched passages 14 into each of the concentrate passages 13A and 13B. The supplied cleaning solution reaches the water supply passage 12 to be diluted with the purified water circulating in the water supply passage 12. When a predetermined amount of the cleaning solution is supplied from the cleaning solution container 25, the water supply solenoid valve 12b is closed and the communicating solenoid valve 42a is opened, so that the cleaning solution is circulated to the upstream side of the water supply passage 12. After the cleaning solution is circulated in the fluid circuit 2 for a predetermined period of time, the main cleaning process is completed.

As described above, the cleaning method of the fluid circuit 2 according to the present invention includes a pre-cleaning process in which a purified water is circulated in the fluid circuit 2 to discharge and replace the dialysis solution remained in the fluid circuit 2 with purified water before a main cleaning process in which a cleaning solution is circulated in the fluid circuit 2, thereby a state of the connections between the concentrate passages 13A and 13B and the couplers 23A and 23B in the cleaning port P which provides a cleaning solution supplying section are checked during the pre-cleaning process.

Therefore, the present invention eliminates the need of restarting a main cleaning process, unlike in the case where an incomplete connection is found during a main cleaning process for supplying a cleaning solution, which involves the risk of insufficient cleaning because the process has been already performed without a supply of a predetermined amount of cleaning solution, and the main cleaning process has to be restarted from the first. Instead, in the present invention, as soon as an incomplete connection is fixed, a pre-cleaning process can be restarted from the point where interrupted by an alert. As a result, there is no waste in cleaning time and cleaning solution, and also an incomplete connection can be detected without fail, which prevents incomplete cleaning due to incomplete connection.

What is claimed is:

1. A method for cleaning a dialysis device which comprises a fluid circuit which is connected to a dialyser, a concentrate passage provided on a fluid supplying side of the fluid circuit which joins the fluid circuit and is connected to a dialysis solution concentrate container, whereby purified water is supplied through a water inlet of the fluid circuit and a dialysis solution concentrate is supplied through the concentrate passage to prepare a dialysis solution in the fluid circuit to be supplied to the dialyser and a cleaning solution supplying section to which the concentrate passage is connected for supplying a cleaning solution to the concentrate passage, comprising the steps of:

during a dialysis treatment, connecting the concentrate passage to the dialysis solution concentrate container to supply the dialysis solution concentrate through the concentrate passage to the fluid circuit;

after the dialysis treatment, during a cleaning process of the fluid circuit, disconnecting the concentrate passage from the dialysis solution concentrate container and connecting the concentrate passage to the cleaning solution supplying section to supply the cleaning solution through the concentrate passage;

performing a pre-cleaning process in which purified water is circulated through the fluid circuit to replace the dialysis solution remaining in the fluid circuit with the purified water, so that a state of the connection between the concentrate passage and the cleaning solution supplying section is checked before the cleaning process in which the cleaning solution is circulated to the fluid circuit and that at the point of time when the fluid circuit is filled with purified water during the pre-cleaning process, a value lower than the conductivity of the dialysis solution is set as a predetermined set value and the conductivity in the fluid circuit is measured, and when the measurement of the conductivity is higher than the predetermined set value, during the pre-cleaning process it is determined that the concentrate passage is connected to the dialysis solution concentrate container.

2. The method for cleaning a dialysis device according to claim 1, further comprising the step of:

determining that the concentrate passage is completely connected to the dialysis solution concentrate container based on a detection of a circulation of the dialysis solution in the fluid circuit, during the pre-cleaning process.

3. The method for cleaning a dialysis device according to claim 1, further comprising the step of:

determining that the concentrate passage is incompletely connected to the cleaning solution supplying section based on a detection of a predetermined amount of gas in the purified water which is circulating in the fluid circuit, during the pre-cleaning process.

\* \* \* \* \*